United States Patent [19]

Hansen et al.

[11] Patent Number: 4,614,730
[45] Date of Patent: Sep. 30, 1986

[54] STABILIZED INSULIN PREPARATIONS AND A PROCESS FOR PREPARATION THEREOF

[75] Inventors: Philip E. Hansen, Copenhagen; Jens J. V. Brange, Klampenborg; Svend Havelund, Hvidovre, all of Denmark

[73] Assignee: Novo Industri A/S, Denmark

[21] Appl. No.: 635,485

[22] Filed: Jul. 31, 1984

Related U.S. Application Data

[63] Continuation of Ser. No. 437,573, Oct. 29, 1982, abandoned.

[30] Foreign Application Priority Data

Oct. 30, 1981 [DK] Denmark .............................. 4786/81
Jul. 20, 1982 [DK] Denmark .............................. 3247/82

[51] Int. Cl.⁴ .............................................. A61K 37/26
[52] U.S. Cl. ........................................ 514/3; 514/970
[58] Field of Search ...................... 514/3, 970

[56] References Cited

U.S. PATENT DOCUMENTS

| | | | |
|---|---|---|---|
| 4,145,410 | 3/1979 | Sears ................................... | 424/178 |
| 4,153,689 | 5/1979 | Hirai et al. ........................... | 424/178 |
| 4,164,573 | 8/1979 | Galinsky .............................. | 514/3 |
| 4,224,179 | 9/1980 | Schneider ............................ | 424/36 |
| 4,229,360 | 10/1980 | Schneider et al. ................... | 424/178 |
| 4,235,871 | 11/1980 | Papahadjopoulos et al. ........ | 424/92 |
| 4,377,567 | 3/1983 | Gehd ................................... | 424/178 |

FOREIGN PATENT DOCUMENTS

32622 7/1981 European Pat. Off. .
2652636 5/1978 Fed. Rep. of Germany .
2952119 9/1981 Fed. Rep. of Germany .

OTHER PUBLICATIONS

Diabetologia 19, 1–9, (1980), Lougheed et al.

*Primary Examiner*—Frederick E. Waddell
*Attorney, Agent, or Firm*—Fidelman, Wolffe & Waldron

[57] ABSTRACT

Isulin solutions physically stabilized by presence of one or more phospholipids, preferably a lecithin. The phospholipid is present in concentration of 10–200 µg/ml.

2 Claims, No Drawings

STABILIZED INSULIN PREPARATIONS AND A PROCESS FOR PREPARATION THEREOF

This application is a continuation of Ser. No. 437,573, filed Oct. 29, 1982, now abandoned.

The present invention relates to novel physically stabilized insulin solutions and to a process for producing such stabilized insulin solutions.

Insulin dissolved in a liquid medium, for example, water, may be stored for several years at ambient temperature, and said preparations are stable within that period of time. If, however, an insulin solution is heated to about 80° C., said insulin will denature within a few minutes, which consequence is designated heat denaturation or polymerization. If an insulin solution is shaken for a few days at a temperature whereat substantially no heat denaturation takes place, for example, at 41° C., another sort of denaturation or polymerization will take place, this sort of denaturation herein being designated interface noncovalent polymerization.

The denaturation is a surface reaction which takes place at the interface between liquid and air (gas). The reaction is believed to start with an adsorption of a mono molecular protein layer to the interface, then denaturation takes place when this protein layer is compressed in connection with an alteration of the interface area. It is unknown how the denaturation process takes place, nor which alterations in the molecule give denaturation although certain hypotheses have been put forward (J. Biol. Chem. 118 (1937), 163, J. Colloid Interface Sci. 70 (1979), 403, J. Colloid Interface Sci. 29 (1969), 66, and J. Colloid Interface Sci. 80 (1981), 393).

Normally, insulin manufacturer, drugstores and patients store insulin preparations at about 5° C. and, apparently, no interface polymerization occurs in insulin preparations although, inevitably, from time to time the insulin preparations are shaken during transport and carriage.

In recent years steadily increasing efforts have been devoted to the development of portable or implantable systems for continuous infusion of insulin. In essence, the mechanical part of a device for continuous insulin delivery comprises such elements as an insulin reservoir, a pumping system and a suitable catheter for delivering insulin to the patient. If the insulin solution is supplied by a syringe the syringe usually functions as the insulin reservoir.

Unfortunately, when insulin in commercially available solutions is placed into such systems, the insulin has been found to exhibit a propensity to undergo interface polymerization at body temperature, then obstruct both mechanical parts and delivery catheters. This characteristic of insulin solutions has proved to constitute a major impediment to further development and clinical application of continuous infusion equipment. Evidently, in any type of continuous delivery equipment, insulin solutions are subjected to movements resulting in interface polymerization. The general shortcomings of prior art insulin preparations in this respect are amply documented in the literature, vide, for example, Diabetologia 19 (1980), 1-9.

To solve this problem it has been proposed to use acidic insulin solutions containing glutamic acid or aspartic acid, vide, Diabetes 30 (1981), 83. However, insulin is chemically unstable in acid, even at below body temperature.

Suggested also is insulin formulations containing non-ionic surfactants, vide German Patent Application No. P 2,952,119. However, non-ionic surfactants could be regarded as undesirable components in drugs intended for parenteral use.

Such inconveniences are overcome by practice of the present invention, which invention provides novel preparations of dissolved insulin wherein the insulin is substantially less prone to interface non-covalent polymerization under conditions prevailing in continuous insulin delivery equipment than has been the case with conventional insulin preparations.

It has now, surprisingly, been found that insulin solutions are stabilized against interface polymerization when at least one phospholipid is present in said solution.

The phospholipids present in insulin solutions according to this invention may be represented by the general formula I

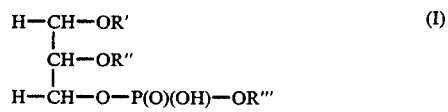

wherein R' and R" are the same or different each representing hydrogen, alkylcarbonyl, alkenylcarbonyl, alkadienylcarbonyl, alkatrienylcarbonyl or alkatetraenylcarbonyl, with the proviso that both R' and R" are not hydrogen, and R''' represents a hydrophilic group such as 2-(trimethylammonio)ethyl, 2-aminoethyl, 2-carboxy-2-aminoethyl, 2,3-dihydroxypropyl or 2,3,4,5,6-pentahydroxycyclohexyl. The phospolipids herein contemplated are phosphoglycerides of choline (lecithins), ethanolamine, serine, glycerol and inositol. The above alkylcarbonyl, alkenylcarbonyl, alkadienylcarbonyl, alkatrienylcarbonyl and alkatetraenylcarbonyl groups contain from 8 to about 22 carbon atoms—in one embodiment from 12 to 22 carbon atoms.

Consequently, the present invention relates to a stabilized insulin solution containing water, dissolved insulin, one or more of the phospholipids of formula I and, optionally, preservative, an agent rendering the insulin solution isotonic, and buffering agents.

A preferred subclass of compounds of formula I is compounds, wherein R' and R" are each alkylcarbonyl. A further preferred subclass of compounds of formula I is compounds, wherein R''' represents 2-(trimethylammonio)ethyl, such compounds being known as lecithins. A still further preference is for compounds of formula I, wherein R' and R" each represent alkylcarbonyl with from about 8 to 16 carbon atoms—or from about 12 to 16 carbon atoms—and R''' represents 2-(trimethylammonio)ethyl. The most preferred subclass of compounds of formula I is compounds wherein R' and R" each represent octanoyl. Compounds of formula I, wherein R' and R" each are octanoyl, are preferred because they do not seem to form liposomes and, furthermore, they do not at lower concentrations, for example, below about 160 μg/ml, seem to form micelles.

The amount of a phospholipid of formula I necessary for stabilizing an insulin solution is in the range of from about 10 to 200 μg/ml, more preferred from about 10 to 100 μg/ml, preferably from about 25 to 75 μg per ml insulin solution, about 30–50 μg/ml being most preferred. The concentration of dissolved insulin in the solutions according to this invention is in the range of from about 5 to 1000 international units (I.U.) per ml or even higher.

Some of the stabilized insulin solutions within the scope of this invention and prepared according to the examples provided hereinafter may contain liposomes. However, such liposomes contain little or no insulin. In stabilized insulin solutions prepared according to practice of this invention, the insulin molecules in solution is essentially outside the closed vesicles of any liposomes present in the solution. Inclusion of some small minor proportion of the insulin content within the liposome vesicles is adventitious; negligible amounts less than 10% and more likely less than 1% of the insulin, will ever be present inside any liposomes in the stabilized insulin solution. The reason why the insulin solutions of this invention are believed to contain no or only a negligible amount of liposomes containing insulin therein is that any ultrasonic treatment of a solution or suspension of a compound of formula I is performed before the addition of insulin.

Liposomes containing insulin as is known to the art, vide, for example, European Patent Application No. 32,622, can be distinguished from practice of this invention by a distinctly different relative proportion of protein to phospholipid, as well as for reason that in compositions of this invention presence of any insulin inside the liposome vesicle is only adventitious.

While the insulin solutions of this invention are intended for parenteral administration, the principal rationale for encapsulating insulin in liposomes is oral administration. One object of liposomes containing insulin therein is to protect the insulin against undesired chemical attack, for example, chemical decomposition of the insulin in the stomach if insulin is administered orally. Thus, the papers concerning liposomes containing insulin do not relate to a physical stabilization of insulin solutions against interface polymerization.

German Offenlegungsschrift No. 2,652,636 relates to a process for stabilization of sensitive proteins by addition of protecting compounds with amphophilic structure. The stabilization according to said Offenlegungsschrift is obtained by encompassing the sensitive protein so as to prevent contact with water.

However, the inventors hereof do not consider insulin a sensitive protein. The object of the present invention is to maintain the insulin in solution, preventing insulin from undergoing interface polymerization.

Characteristically, concentrations of phospholipid in the solutions of this invention, i.e., 10 $\mu$g–200 $\mu$g per ml, are far lower than is suggested for liposomes containing insulin and the proportions of insulin to phospholipid are far higher. The weight ratio between the phospholipid and insulin is in the range of 1:5 to 1:10,000 preferably 1:10 to 1:1000. When insulin is encapsulated in liposomes, the ratio may be about 1:0.01. Characteristic practice of this invention is employment of the least phospholipid effective for stabilization.

It is known that phospholipides are able to form monomolecular layers at a liquid/air interface. Furthermore, it is known that it may be difficult for protein molecules to penetrate such monomolecular phospholipid layers (Biol Chem. J. 193 (1981) 607).

Stabilization against interface polymerization is believed caused by preventing migration of insulin molecules to the air/water interface despite shaking with then only enough of phospholipide being needed in the solution to generate and preserve a complete monomolecular phospholipid layer at the interface of the solution. Accordingly, very low concentrations of phospholipid should be and have been found to be necessary to obtain a stabilizing effect.

Thus, it is believed that the stabilizing effect of phospholipids with respect to interface denaturation is due to the ability of the phospholipid molecules to prevent a formation of a monomolecular protein layer in the interface.

The insulin solutions according to this invention may contain bovine, porcine or human insulin.

The insulin solutions may contain preservatives, an agent rendering the solution isotonic and a buffering agent. Presence of these substances have no effect on the phospholipid or the stabilizing consequence resulting from inclusion of the phospholipid. Indeed, stabilization of insulin according to practice of the invention of Ser. No. 356,343 filed Mar. 9, 1982, through presence of controlled quantities of calcium ions or magnesium ions in the insulin solution may be improved upon by inclusion of 10$\mu$g–200 $\mu$g per ml of phospholipid.

In a preferred embodiment the insulin solution of this invention contains zinc. However, the amount of zinc should be chosen so that no precipitation occurs. A good stability against interface polymerization is obtained in insulin solutions wherein the ratio between the molar concentration of zinc ions at the disposal of insulin and the molar concentration of insulin being calculated as hexamer insulin is in the range from about 1.5 to 4.6, preferably from about 3 to 4.5, most preferred from about 3.6 to 4.3. Preferred zinc salts are soluble zinc salts such as zinc acetate or chloride. If the insulin solution of this invention contains compounds which form complexes with insulin, such as an amino acid, for example, glycin or histidin, or a hydroxy carboxylic acid, for example, citric acid, only a part of the total zinc content is at the disposal of insulin.

An exemplary mode of preparing the insulin solutions of this invention comprises dissolving crystalline zinc insulin, for example, a highly purified grade of insulin, such as "monocomponent" insulin, vide British Patent No. 1,285,023, in water in the presence of acid, for example hydrochloric acid. An aqueous solution of preservative, for example, phenol, an alkyl phenol, such as cresol, or methyl p-hydroxybenzoate, is prepared separately. If desired, preservative solution may also contain an agent such as sodium chloride or glycerol for rendering the final insulin solution isotonic. Furthermore, the preservative solution may contain buffering agents, such as sodium orthophosphate, sodium citrate, sodium acetate or TRIS (tris(hydroxymethyl)aminomethane). The resulting preservative solution is then added to the acid insulin solution followed by addition of a base, for example, a sodium hydroxide solution, to adjust the pH value of the insulin solution to neutrality. Within the context of this invention neutrality is to be understood as a pH value in the range of from about 6.5 to about 8. The phospholipid of formula I is added in solution or colloid solution form, by dissolving or suspending phospholipid of formula I in water and, if necessary, subjecting said suspension or mixture to ultrasonic treatment. The phospholipid solution may, if desired, contain the buffering agent and preservative to be incorporated into the final insulin solution. After mixing in the phospholipid, the pH value of the insulin preparation may be readjusted to neutrality if necessary. Finally, the resulting insulin solution is made up to the calculated volume by addition of water, then sterilized by filtration and, subsequently, transferred aseptically to sterile vials which are then sealed.

The present invention also comprises a process for preparing the solutions according to this invention which process is characterized by mixing insulin with a phospholipid of formula I and optionally with a preservative, an agent rendering the solution isotonic and a buffering agent, whenever presence of these optional materials is desired, in the presence of water.

Some compounds of formula I are known and the remaining compounds of formula I may be prepared in analogy with the preparation of known compounds.

STABILITY TEST

In order to determine the stability of insulin solutions against interface polymerization, said solutions are subjected to a stability test under forced conditions in the following manner:

Vials (of 12.5 ml capacity) containing the test sample (10 ml), each provided with a rubber cap are placed vertically on a shaking platform (supplied by HETO, Denmark) which is totally immersed in a water bath kept at 41° C. +/−0.1° C. The platform is subjected to horizontal rocking movements with a frequency and amplitude of 100 rpm and 50 mm, respectively.

The opalescence of the test samples is monitored at regular time intervals on a "Fischer DRT 1000 nephelometer" (supplied by Fischer, Canada). Interface polymerization is considered to have taken place, when the turbidity exceeds 10 nephelometric turbidity units (NTU).

The stability factor is calculated as the ratio of the interface polymerization time of the test sample to that of a control sample prepared in the same manner as the test sample when no phospholipid of formula I is added to the control sample.

Detailed practices of the present invention are furnished by way of the following examples which, however, should not be constructed so as to limit the scope of the invention.

EXAMPLE 1

500 mg of semisynthetic human insulin were dissolved in 10 ml of 0.045N hydrochloric acid and 359 mg of methyl p-hydroxybenzoate dissolved in 300 ml of distilled water were added. Furthermore, 476 mg of sodium acetate trihydrate, 2,46 g of sodium chloride and 4.73 ml of a 0.2N sodium hydroxide solution dissolved in 15 ml of distilled water were added. 9 mg of dimyristoyl,L-alphaphosphatidyl-choline were suspended in 10 ml of a solution of 70 mg of sodium chloride, 13.6 mg of sodium acetate and 10 mg of methyl p-hydroxybenzoate in distilled water. Nitrogen was bubbled through the slurry which was subjected to ultrasonic treatment in an ultrasonic bath for 2 hours. The resulting colloid solution was added to the insulin solution with stirring. The pH-value was adjusted to 7.45 with 0.2N hydrochloric acid or a 0.2N sodium hydroxide solution and distilled water was added ad 350 ml. The stability factor of the resulting insulin solution was above 125.

EXAMPLE 2

9.65 g of porcine insulin were dissolved in 400 ml of 0.02N hydrochloric acid and 5.0 g of crystalline phenol and 40 g of anhydrous glycerol were added and, furthermore, distilled water was added ad 2200 ml. The pH value was adjusted to 7.45 with a 0.2N sodium hydroxide solution. 125 mg of distearoyl,L-alphaphosphatidylcholine were dissolved by gentle heating in 2 ml of ethanol (96%) and were via a hypodermic syringe injected into 100 ml of distilled water having a temperature of 70° C. with vigorous stirring. The resulting turbid solution was subjected to ultrasonic treatment with a high energy ultrasound probe for 15 minutes and the resulting colloid solution was added to the insulin solution with stirring and distilled water was added ad 2500 ml. The pH value was, if necessary, readjusted to 7.45. The stability factor was above 30.

EXAMPLES 3 to 8

Insulin solutions were prepared in analogy with the process described in Example 1, provided that the phospholipids used were lecithins wherein the hydrophobic moieties, i.e., R' and R", which are the same as those stated in Table I. Also, the results appear in Table I.

TABLE I

| Example No. | R' and R" | Insulin species | Stability factor |
|---|---|---|---|
| 3 | myristoyl | porc | above 120 |
| 4 | palmitoyl | porc | 104 |
| 5 | stearoyl | porc | above 117 |
| 6 | lauroyl | human | above 133 |
| 7 | myristoyl | human | above 133 |
| 8 | palmitoyl | human | 75 |

EXAMPLE 9

An insulin solution was prepared in analogy with the process described in Example 1; the phospholipid used was egg lecithin and the insulin used was porcine insulin. The stability factor was 96.

EXAMPLES 10 to 14

Insulin solutions were prepared in analogy with the process described in Example 1, prepared from porcine insulin at concentrations stated in Table II. Also, the results appear in Table II.

TABLE II

| Example No. | Insulin, I.U./ml | Stability factor |
|---|---|---|
| 10 | 20 | above 120 |
| 11 | 40 | above 120 |
| 12 | 100 | 97 |
| 13 | 200 | 79 |
| 14 | 500 | 53 |

EXAMPLE 15

1.50 g of porcine insulin were dissolved in 6.5 ml of 0.2N hydrochloric acid and water was added ad 50 ml. 1.0 g of methyl phydroxybenzoate and 1.78 g of sodium phosphate were dissolved in 900 ml of distilled water and the insulin solution was added. The pH value was adjusted to 7.45 with a 0.2N sodium hydroxide solution. A colloid dimyristoyl,L-alphaphosphatidylcholine solution prepared in analogy with the process described in Example 2 was added together with distilled water ad 1000 ml. The stability factor was above 30.

EXAMPLE 16

An insulin solution was prepared in analogy with Example 15, provided that the solution contained 20 I.U. insulin/ml. The stability factor was above 17.

EXAMPLE 17

An insulin solution was prepared in analogy with Example 15, provided that the insulin concentration was 500 I.U./ml, and the dimyristoyl,L-alpha-phosphatidylcholine content was 50 μg/ml. The stability factor was above 30.

EXAMPLES 18 to 20

Insulin solutions were prepared in analogy with the process described in Example 2, provided that dimyristoyl,L-alpha-phosphatidylcholine was used in the final concentration stated in Table III. Also, the results appear in Table III.

TABLE III

| Example No. | Dimyristoyl compound, μg/ml | Stability factor |
|---|---|---|
| 18 | 1 | 1.3 |
| 19 | 10 | 1.8 |
| 20 | 50 | above 33 |

EXAMPLE 21

Dioctanoyl,L-alpha-phosphatidylcholine was dissolved in distilled water and was, in a concentration of 30 μg per ml, added to an insulin solution prepared as in Example 1. The stability factor was above 63. This Example and the following Example describe preferred modes of the invention.

EXAMPLE 22

3.65 g of semi-synthetic human insulin was dissolved in 100 ml of 0.02 N hydrochloric acid and 2.0 g of crystalline phenol. 16 g of anhydrous glycerol and 0.3 ml of a 4% zinc chloride solution were added and, then distilled water was added at 900 ml. The pH value was adjusted to 7.45 with a 0.2 N sodium hydroxide solution. 50 mg of dioctanoyl,L- alpha-phosphatidylcholine dissolved in distilled water was added to the insulin solution. Distilled water was added ad 1000 ml. The stability factor was 65.

What is claimed is:

1. A process for producing an insulin solution of pH within the range of about pH 6.5–8 stabilized against interface polymerization, stabilization being ascertainable by submitting the insulin solution to shaking and measuring the time before opalescence appears in the insulin solution; said stabilized insulin solution being adapted for parenteral administration by portable or implantable system for continuous infusion of insulin, which process comprises mixing insulin with a phospholipid in a phospholipid to insulin weight ratio of 1:5 to 1:10,000, the phosphlolipid formula being:

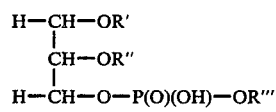

wherein R' and R" are the same or different each being selected from the group consisting of hydrogen, higher alkylcarbonyl, alkenylcarbonyl, alkadienylcarbonyl, alkatrienylcarbonyl and alkatetraenylcarbonyl, with the proviso that both R' and R" are not hydrogen, and R'" is selected from the group consisting of 2-(trimethylammonio)ethyl, 2-aminoethyl, 2-carboxy-2-aminoethyl, 2,3-dihydroxpropyl and 2,3,4,5,6-pentahydroxycyclohexyl, in the presence of water, and optionally with a zinc salt, a preservative, an agent rendering the insulin solution isotonic, and a buffering agent so as to obtain a concentration of phospholipid of 10–200 μg/ml of stablilized insulin solution, the insulin in solution being essentially outside any liposomes formed by said phospholipid.

2. The process of claim 1 further comprising preparing said phospholipid solution by adding the phospholipid to water then subjecting the resulting mixture to ultrasonic treatment, whereafter the phospholipid solution is added to the insulin solution.

* * * * *